Figure 1:
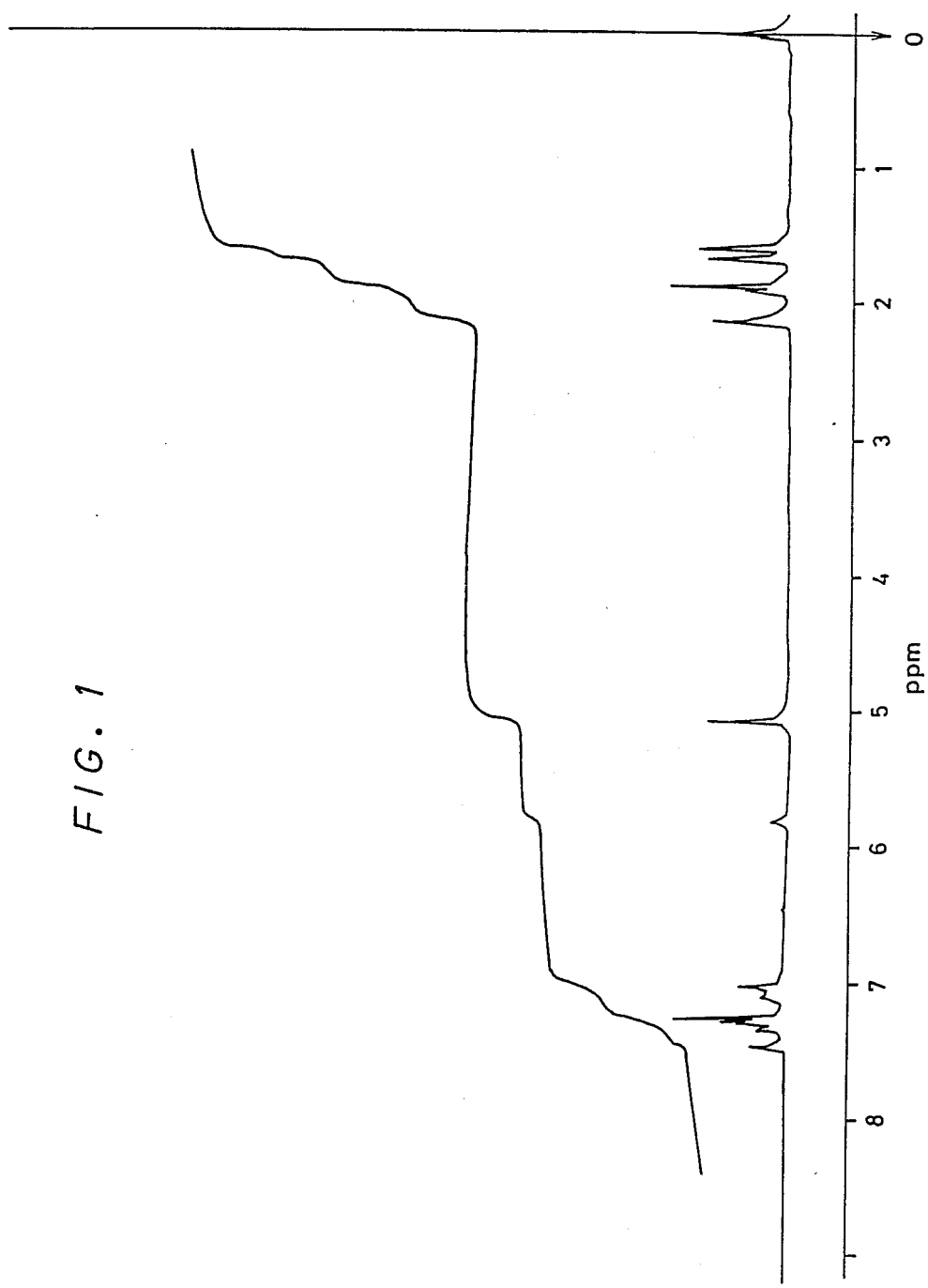

United States Patent [19]

Kuwano et al.

[11] Patent Number: 4,812,473

[45] Date of Patent: Mar. 14, 1989

[54] 1,5-DISUBSTITUTED IMIDAZOLES AS INHIBITORS OF JUVENILE HORMONE

[75] Inventors: Eiichi Kuwano; Ryuko Takeya; Morifusa Eto, all of Fukuoka; Shoji Asano, Tokushima, all of Japan

[73] Assignee: Earth Chemical Co., Ltd., Ako, Japan

[21] Appl. No.: 141,361

[22] PCT Filed: Mar. 24, 1987

[86] PCT No.: PCT/JP87/00180
§ 371 Date: Nov. 23, 1987
§ 102(e) Date: Nov. 23, 1987

[87] PCT Pub. No.: WO87/05899
PCT Pub. Date: Oct. 8, 1987

[30] Foreign Application Priority Data

Mar. 24, 1986 [JP] Japan .................. 61-66890

[51] Int. Cl.⁴ .................. A61K 31/415; C07D 233/58
[52] U.S. Cl. .................. 514/396; 548/335; 548/346
[58] Field of Search ................ 548/335, 346; 514/396

[56] References Cited
PUBLICATIONS

Kuwano, E. et al., *Agric. Biol. Chem.*, 49(2), 483–486 (1985).

*Primary Examiner*—Richard A. Schwartz
*Attorney, Agent, or Firm*—Armstrong, Nikaido Marmelstein & Kubovcik

[57] ABSTRACT

The present invention provides a 1,5-disubstituted imidazole represented by the formula (1)

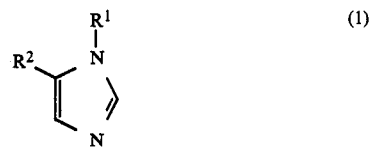

wherein $R^1$ is a lower alkyl group, a cycloalkyl group or a phenyl lower alkyl group, and $R^2$ is a 2,6-dimethyl-1,5-heptadienyl group or a 2,6-dimethylheptyl group, except for a compound wherein $R^1$ is a phenyl lower alkyl group and $R^2$ is a 2,6-dimethyl-1,5-heptadienyl group, and a salt thereof, a process for their preparation and an active agent able to inhibit the activity of the juvenile hormone.

6 Claims, 15 Drawing Sheets

1,5-DISUBSTITUTED IMIDAZOLES AS INHIBITORS OF JUVENILE HORMONE

TECHNICAL FIELD

The present invention relates to 1,5-disubstituted imidazoles and salts thereof, a process for their preparation and an agent having an activity to be effective against the juvenile hormone.

BACKGROUND ART

The growth and reproduction of arthropods such as insects and the like are controlled by their hormones. For example, chiefly their two hormones, i.e., juvenile hormone (JH) and moulting hormone (MH), participate in the ecdysis and metamorphosis of larvae during their growth. If the relative balance of these hormones in insects' living body could be disturbed, the insects' normal development could be retarded. Accordingly if this action is utilized, noxious insects to be controlled could be selectively killed without affecting humans and other animals. From this viewpoint, these hormones and susbstances having similar activities have been variously investigated and developed as a new low-toxicity vermin-repellent or -killing agent and are attracting attention. Said JH is a hormone related to, e.g. insects' development, reproduction and dormancy. For example, it is known that the larvae from which the corpus allatum capable of secreting the juvenile hormone has been removed become a pupa or imago without undergoing repeated normal ecdysis (premature metamorphosis). If a substance having an action to inhibit the activity of the juvenile hormone (anti-JH active substance) is discovered, the substance could similarly suppress the larva's normal growth, cause the larva's premature metamorphosis, damage the imago's reproductive function and exhibit an ovicidal activity. Since the premature metamorphosis thus occurring results in small-size larvae and in the reduction of larval period, the extent of damage inflicted by the larvae of noxious insects on agricultural products will be diminished and the number of noxious insects will be decreased.

OBJECT OF THE INVENTION

From such viewpoints, the present inventors conducted extensive research to provide an anti-JH active substance which can be used as a new hormone-type vermin-repellent or -killing agent and successfully synthesized 1,5-disubstituted imidazoles represented by the formula (A) shown below to find that these compounds and salts thereof can fulfill said object. Based on this finding, the inventors have accomplished an invention, which was then applied for a patent (Patent Application No. Showa 59-186015).

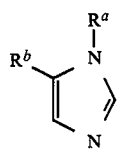

wherein $R^a$ is a citronellyl group or a phenyl lower alkyl group optionally having on the phenyl ring a halogen atom, a lower alkyl group or a lower alkoxy group as a substituent, and $R^b$ is a 2,6-dimethyl-1,5-heptadienyl group, a phenyl group or a styryl group, with the proviso that when $R^a$ is a citronellyl group, $R^b$ must not be a phenyl group.

CONSTRUCTION OF THE INVENTION

As a result of continued research, the inventors have accomplished the present invention which concerns with 1,5-disubstituted imidazoles of the formula (1) as shown below and salts thereof, a process for their preparation and an agent containing the compound and having an activity to be effective against the juvenile hormone.

wherein $R^1$ is a lower alkyl group, a cycloalkyl group or a phenyl lower alkyl group, and $R^2$ is a 2,6-dimethyl-1,5-heptadienyl group or a 2,6-dimethylheptyl group, except for a compound wherein $R^1$ is a phenyl lower alkyl group and $R^2$ is a 2,6-dimethyl-1,5-heptadienyl group.

The term "lower alkyl group" used herein refers to a straight chain or branched chain alkyl group having 1 to 6 carbon atoms. Examples of the lower alkyl group are methyl, ethyl, propyl, isopropyl, butyl, isobutyl, sec-butyl, tert-butyl, amyl, isoamyl, hexyl and the like. The phenyl lower alkyl groups include those with the alkyl moeity which is a straight chain or branched chain alkyl group having 1 to 6 carbon atoms such as benzyl, phenethyl, phenylpropyl, phenylbutyl, phenylhexyl and the like. The term "cycloalkyl group" is intended to denote the cycloalkyl groups having 3 to 8 carbon atoms among which a cyclopentyl group and a cyclohexyl group are preferred.

Preferred classes of 1,5-disubstituted imidazoles of the present invention represented by the formula (1) are the compounds represented by the following formulas.

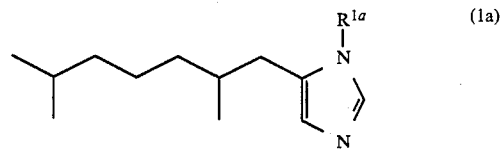

wherein $R^{1a}$ is a phenyl lower alkyl group, and

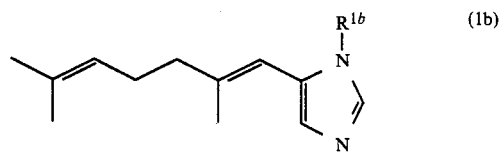

wherein $R^{1b}$ is a lower alkyl group or a cycloalkyl group.

Typical of the compounds of the formula (1a) is 1-benzyl-5-(2,6-dimethylheptyl)imidazole.

Given below are examples of compounds of the formula (1b) which are effective in repelling and killing household noxious insects to be described later such as cockroaches, flies, mosquitoes, fleas, acarids (Tyrophagus putrescentiae, Dermatophagoides farinae, Cheyletus eruditus), etc., hence preferable:
1-methyl-5-(2,6-dimethyl-1,5-heptadienyl)imidazole,
1-ethyl-5-(2,6-dimethyl-1,5-heptadienyl)imidazole,
1-propyl-5-(2,6-dimethyl-1,5-heptadienyl)imidazole,
1-butyl-5-(2,6-dimethyl-1,5-heptadienyl)imidazole,
1-amyl-5-(2,6-dimethyl-1,5-heptadienyl)imidazole,
1-hexyl-5-(2,6-dimethyl-1,5-heptadienyl)imidazole,
1-isopropyl-5-(2,6-dimethyl-1,5-heptadienyl)imidazole,
1-isobutyl-5-(2,6-dimethyl-1,5-heptadienyl)imidazole,
1-sec-butyl-5-(2,6-dimethyl-1,5-heptadienyl)imidazole,
1-isoamyl-5-(2,6-dimethyl-1,5-heptadienyl)imidazole,
1-cyclopentyl-5-(2,6-dimethyl-1,5-heptadienyl)imidazole, and
1-cyclohexyl-5-(2,6-dimethyl-1,5-heptadienyl)imidazole.

The process for preparing the compounds of the present invention will be described below in detail.

The compounds of the present invention represented by the formula (1b) can be prepared, for example, by the process as shown in the following reaction scheme.

<Reaction Scheme 1>

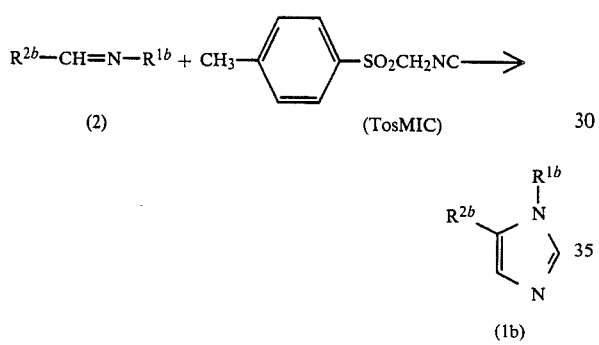

wherein $R^{1b}$ is as defined above, and $R^{2b}$ is a 2,6-dimethyl-1,5-heptadienyl group.

According to Reaction Scheme 1, the imine compound (2) is reacted with the tosylmethylisocyanide (TosMIC) to give the compound (1b). The foregoing reaction is conducted in a solvent such as methanol or like alcohols, dimethoxyethane or like ethers in the presence of an inorganic base such as potassium carbonate, sodium carbonate or the like, or an organic base such as isopropylamine, t-butylamine or the like, preferably at or around room temperature. While the ratios of starting compounds used are not specifically limited, usually at least one mole, preferably about 1 to about 1.5 moles, of tosylmethylisocyanide (TosMIC) and at least one mole, preferably about 2 to about 3 moles, of the basic compound are used per mole of the imine compound (2).

The imine compound (2) serving as the starting compound is prepared by reacting the corresponding aldehyde with the corresponding amine.

Said process is advantageous in producing the contemplated compound in a relatively high yield without a tendency to produce isomers as by-products.

The compound of the present invention represented by the formula (1a) can be prepared by the process as illustrated below in Reaction Scheme 2 from a compound of the following formula (3) obtained by the same process as shown above in Reaction Scheme 1.

<Reaction Scheme 2>

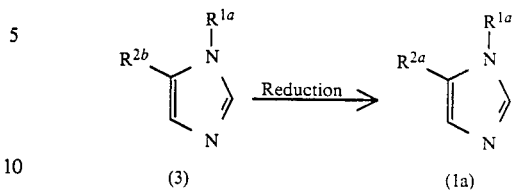

wherein $R^{1a}$ and $R^{2b}$ are as defined above, and $R^{2a}$ is a 2,6-dimethylheptyl group.

According to Reaction Scheme 2, the compound of the formula (3) is subjected to catalytic reduction reaction to give the compound of the present invention represented by the formula (1a). The catalytic reduction is effected in the usual manner, for example, using a catalyst commonly used for catalytic reduction such as palladium-carbon or the like. The reaction will be set forth in detail in Examples to be described later.

After completion of the reactions as shown in Reaction Schemes 1 and 2, the reaction product can be isolated and purified by the usual separation or purification methods such as ether extraction, distillation, column chromatography or the like.

The compound of the present invention thus obtained can be easily made into an acid addition salt by being subjected to addition reaction in the usual manner using a suitable acidic compound. Examples of acidic compounds useful in forming an acid addition salt are inorganic acids such as hydrochloric acid, sulfuric acid, phosphoric acid, hydrobromic acid and the like, and organic acids such as maleic acid, fumaric acid, malic acid, tartaric acid, citric acid, benzoic acid, benzenesulfonic acid and the like.

The compounds of the present invention and the salts thereof thus obtained have an activity to inhibit the action of juvenile hormone (anti-JH activity, premature activity), are unlikely to harm the human body and the like, highly safe and thus useful as an anti-JH active agent, particularly as a hormone-type agent for repelling or killing noxious insects as stated above. The compounds of the present invention are also useful as a synergist for insecticides and are able to exhibit sustained insecticidal effects.

For use as the anti-JH active agent or vermin-repellent or -killing agent, the compound of the present invention and a salt thereof are applied as they are or in the form of a suitable preparation such as a solution, emulsion, suspension, powder, paste, capsules, granules or the like. The preparation is applied by the usual method such as applying atomized preparation, spraying, spreading, etc. over, e.g. noxious insects required to be repelled or killed, their habitats, agricultural products and the products' cultivation areas in which vermins should be controlled.

The preparation is produced by conventional methods, for example, by mixing the compound of the present invention or a salt thereof with an extender, i.e. liquid or solid carrier and when required, liquefied gas (LPG, DME or the like), propellant such as freon, surfactant (emulsifier, foaming agent, dispersant or the like) and the like. Examples of useful liquid carriers are aromatic hydrocarbons such as xylene, toluene, benzene, alkylnaphthalene and the like; chlorinated aromatic or aliphatic hydrocarbons such as chlorobenzene, chloroethylene, methylene chloride and the like; mineral oil fractions; alcohols such as butanol, glycol and the like, ethers and esters thereof; ketones such as acetone, methyl ethyl ketone, methyl isobutyl ketone, cyclohexanone and the like; polar solvents such as dimethylformamide, dimethyl sulfoxide, acetonitrile, water and the like; etc. Examples of solid carriers are powders of natural minerals such as kaolin, clay, talc, chalk, quartz, attapulgite, montmorillonite, diatomaceous earth and the like, powders of synthetic minerals such as silicic acid, alumina, silicate and the like.

Examples of emulsifiers, foaming agents and dispersants are polyoxyethylene-fatty acid ester, polyoxyethyelene-fatty alcohol ether, alkylaryl polyglycol ether, alkylsulfonate, alkylsulfate, arylsulfonate, albumin hydrolysis products, lignin, sulfite waste liquor, methyl cellulose, etc.

The compound of the present invention and a salt thereof can be used conjointly with other insecticides or like active compounds. Examples of useful active compounds are as follows:

3-allyl-2-methylcyclopenta-2-ene-4-one-1-yl dl-cis/-transchrysanthemate (available under "allethrin"), 3-allyl-2-methylcyclopenta-2-ene-4-one-1-yl d-cis/-transchrysanthemate (available under the trademark "Pynaminforte", product of SUMITOMO CHEMICAL CO., LTD.), d-3-allyl-2-methylcyclopenta-2-ene-4-one-1-yl d-cis/-transchrysanthemate (available under the trademark "Exlim", product of SUMITOMO CHEMICAL CO., LTD.), 3-allyl-2-methylcyclopenta-2-ene-4-one-1-yl d-transchrysanthemate (available under "bioallethrin"), N-(3,4,5,6-tetrahydrophthalimide)methyl dl-cis/-transchrysanthemate (available under "phthalthrin"), 5-benzyl-3-furylmethyl d-cis/trans-chrysanthemate (available under "resmethrin"), 2-methyl-5-(2-propargyl)-3-furylmethyl chrysanthemate (available under "furamethrin"), 3-phenoxybenzyl 2,2-dimethyl-3-(2', 2' -dichloro) vinyl-cyclopropanecarboxylate (available under "permethrin"), 3-phenoxybenzyl d-cis/trans-chrysanthemate (available under "phenothrin"), α-cyano-3'-phenoxybenzyl-α-isopropyl-4-chlorophenyl acetate (available under "fenvalerate"), O,O-dimethyl O-(2,2-dichloro)vinylphosphate (DDVP), O,O-dimethyl O-(3-methyl-4-nitrophenyl)thionophosphate (Sumithion), O,O-diethyl O-2-isopropyl-4-methyl-pyrimidyl-(6)thiophosphate (Diazinon), O,O-dimethyl S-(1,2-dicarboethoxyethyl)-dithiophosphate (Malathion), O-isopropoxyphenyl methylcarbamate (Baygon), O-(4-bromo-2,5-dichlorophenyl) O,O dimethylphosphorothioate (bromophos).

Generally the preparation contains 0.1 to 95% (% by weight, the same hereinafter), preferably 0.1 to 90%, of the compound of the present invention and/or a salt thereof. The preparation can be further diluted for practical application. The concentration of the compound of the present invention or a salt thereof to be used as the active component is widely variable over a wide range and can be in the range of generally 0.0001 to 10%, preferably 0.01 to 1%.

The insects to be repelled or controlled by application of the compound of the present invention are not limited at all insofar as insects' growth and reproduction are controllable by their hormones. These insects include a wide variety of those such as acarids, nematodes and all kinds of arthropods harmful to humans and beasts. Typical examples of said noxious insects are as follows.

Noxious insects in the order Lepidoptera include *Plutella maculipennis, Leucoptera coffeella, Yponomeuta malinellus, Argyresthia conjugella, Sitotroga cerealella, Phthorimaea operculella, Capua reticulana, Sparganothis pilleriana, Cacoecia murinana, Tortrix viridana, Clysiana ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, ChIo suppressalis, Galleria mellonella, Malacosoma neustria, Dendrolimus pini, Thaumatopoea pityocampa, Phalera bucephala, Cheimatobia brumata, Hibernia defoliara, Bupalus piniarus, Hyphantria cunea, Agrotis segetum, Agrotis ipsilon, Barathra brassicae, Cirphis unipuncta, Prodenia litura, Laphygma exigua, Panolis flammea, Earias insulana, Plusia gamma, Alabama argillacea, Lymantria dispar, Lymantria monacha, Pieris brassicae, Aporia crataegi, Antheraea yamamai, Caligula boisduvalii jonasii, Dictyoploca japonica*, etc.

Noxious insects in the order Coleoptera include *Blitophaga undata, Melanotus communis, Limonius californicus, Agriotes lineatus, Agriotes obscurus, Agrilus sinuatus, Maligethes aneneus, Atomaria linearis, Epilachna varivestris, Phyllopertha horticola, Popillia japonica, Melolontha melolontha, Melolontha hippocastani, Amphimallus solstitialis, Crioceris asparagi, Lama malanopus, Leptinotarsa decemlineata, Phaedon cochleariae, Phyllotreta memorum, Chaetocema tibialis, Psylloides chrysocephala, Diabrotica undecimpunctala, Cassida nebulosa, Bruchus lentis, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus, Blastophagus piniperda*, etc.

Noxious insects in the order Diptera include *Lycoria pectoralis, Mayetiola destructor, Dasyneura brassicae, Contarinia tritici, Haplodiplosis squstrie, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coaractata, Phorbia antiqua, Phorbia brassti, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata, Hypoderma lineata*, etc.

Noxious insects in the order Hymenoptera include *Athalia rosae, Haplocampa minuta, Monomorium pharaonis, Solenopsis geminata, Atta sexdens*, etc.

Noxious insects in the order Heteroptera include *Nezara viridula, Eurygaster integriceps, Blissus leucopterus, Dysdercus cingulatus, Dysdercus intermedius, Piesma quuadrata, Lygus pratensis*, etc.

Noxious insects in the order Homoptera include *Perkinsiella saccharicida, Nilaparvata lugens, Empoasca fabae, Psylla mali, Psylla piri, Trialeurodes vaporariorum, Aphis fabae, Aphis pomi, Aphis samouci, Aphidula nasturlaus, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolami, Acyrthosiphon onobrychis, Macrosiphon*

*rosae, Megoura viciae, Schizoneura lanuginosa, Pemphigus bursarius, Dreyfusia nordmannianae, Dreyfusia piceae, Adelges laricis, Viteus vitifolii,* etc.

Noxious insects in the order Isoptera include *Reticulitermes lucifugus, Calotermes flavicollis, Leucotermes flavipes, Termes natalensis,* etc.

Noxious insects in the order Orthoptera include *Porficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femurrubrum, Blatta orientalis, Blattella germanica, Periplaneta americana, Blabera gigantea,* etc.

Noxiuous insects in the order Acarina include *Ornithonyssus bacoti, Dermanyssus gallinae, Ornithonyssus sylviarum, Macrocheles muscaedomesticae, Hoshikadania konoi, Carpoglyphus lactis, Trombicula akamushi, Trombicula scutellaris, Tyrophagus putrescentiae, Dermatophagoides farinae, Dermatophagoides scheremetewskyi, Cheyletidae, Tetranychidae, Tarsonemidae, Pyemotidae, Glycyphagidae, Oribatei,* etc.

Exemplary of Nematoda are *Meloidogyne incognita, Meloidogyne hapla, Meloidogyne javanica, Heterodera rostochiensis, Heterodera schachtii, Heterodera avenae, Heterodera glycines, Heterodera trifolii, Ditylenchus dipsaci, Ditylenchus destructor, Pratylenchus neglectus, Pratylenchus penetrans, Pratylenchus goodeyi, Pratylenchus curvitatus, Tylenchorhynchus dubius, Tylenchorhynchus claytoni, Rotylenchus robustus, Heliocotylenchus multicinctus, Rodopholus similis, Belonolaimus longicaudatua, Longidorus elongatus, Trichodorus primitivus,* etc.

EXAMPLES

To describe the present invention in greater detail, we give below as reference examples preparation examples illustrative of preparation of starting compounds for producing the compound of the present invention and as working examples preparation examples illustrative of preparation of the compound of the present invention.

In the examples, the drawings referred to are as follows.

Figure 2:
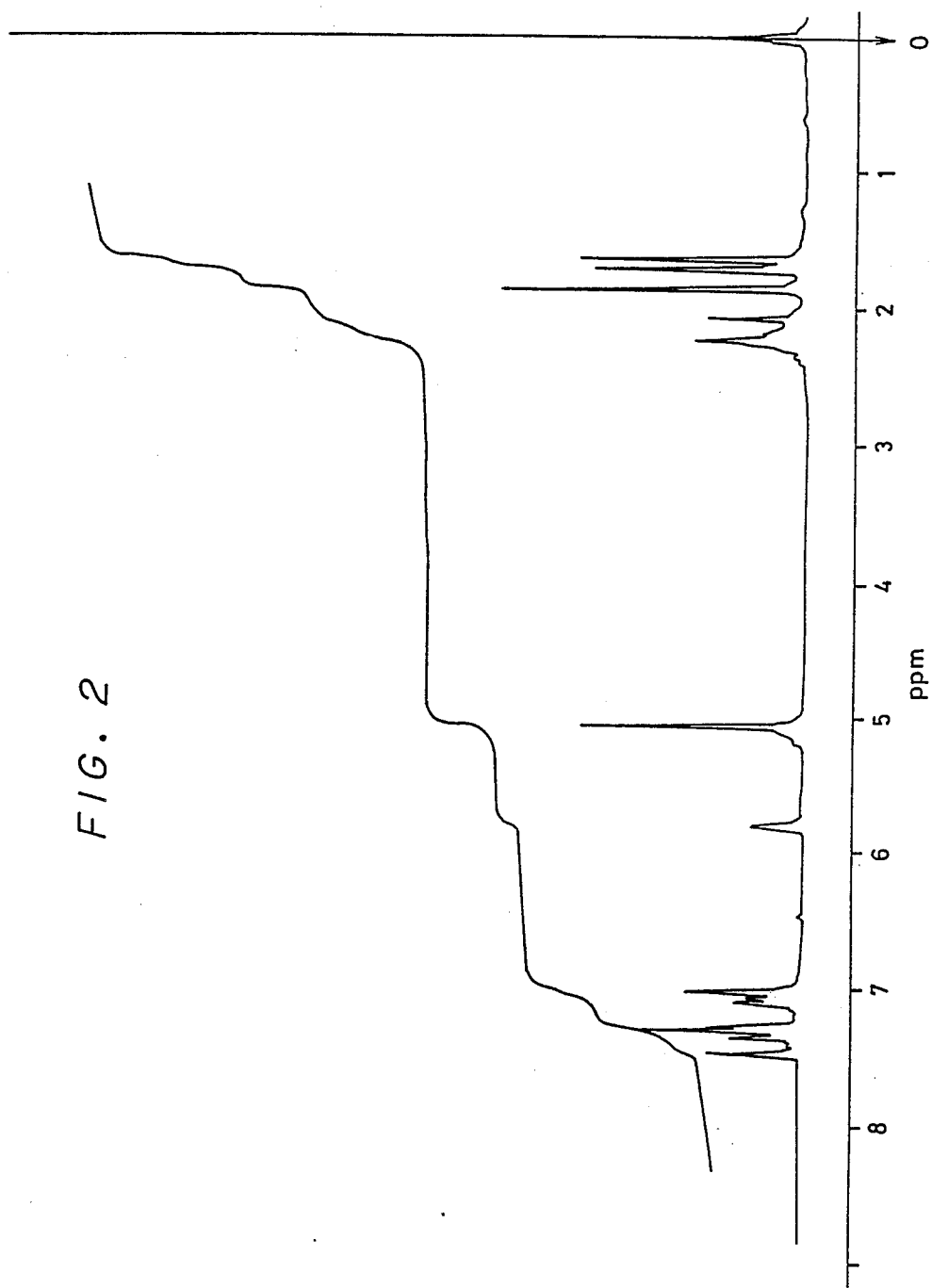

FIGS. 1 and 2 are graphs showing the nuclear magnetic resonance spectrum analysis of starting compounds obtained in Reference Example 1. FIGS. 3 to 15 are graphs showing the nuclear magnetic resonance spectrum analysis of the compounds of the present invention obtained in Examples 1 to 13.

REFERENCE EXAMPLE 1

Preparation of 1-benzyl-5-[(E)-2,6-dimethyl-1,5heptadienyl]imidazole (Compound 1) and 1-benzyl-5-[(Z) 2,6-dimethyl-1,5-heptadienyl]imidazole (Compound 2)

A 3.2 g quantity of benzylamine and 4.5 g of citral were dissolved in 30 ml of dichloromethane. To the solution was added 15 g of anhydrous magnesium sulfate and the mixture was refluxed with heating for 3 hours. After filtering off magnesium sulfate, the filtrate was concentrated under reduced pressure, giving an imine compound, which was then dissolved in 30 ml of dried methanol. Anhydrous potassium carbonate (15 g) was added to the solution, followed by addition of 7.5 g of p-toluenesulfonylmethylisocyanide (TosMIC) to the mixture. The mixture was refluxed with heating for 3 hours. After cooling, the solvent was distilled off from the reaction mixture under reduced pressure, and the residue was extracted with ether. After washing the ether layer with a saline solution, the layer was dried over anhydrous sodium sulfate. The solvent was distilled off under reduced pressure and the residue was purified by silica gel column chromatography. Elution was conducted using, first, hexane-ether (1:1) and then ether. The compound 2 was eluted with hexane-ether (1:1) and the compound 1 with ether. The solvent was distilled off from each eluate under reduced pressure, giving each contemplated compound.

[Compound 1]

Yield 25%,

Elementary analysis ($C_{19}H_{24}N_2$)

| Elementary analysis ($C_{19}H_{24}N_2$) | | | |
|---|---|---|---|
| | C | H | N |
| Found (%) | 81.43 | 8.57 | 10.00 |
| Calcd. (%) | 81.23 | 8.67 | 10.02 |

Result of ultraviolet absorption spectrum (UV) analysis

λmax ($CH_3OH$) 253 nm (ξ14500)

Result of nuclear magnetic resonance spectrum ($^1$H-NMR) analysis

FIG. 1 shows the result obtained using TMS as an internal standard substance in $CDCl_3$.

[Compound 2]

Yield 10%

| Elementary analysis ($C_{19}H_{24}N_2$) | | | |
|---|---|---|---|
| | C | H | N |
| Found (%) | 81.43 | 8.57 | 10.00 |
| Calcd. (%) | 81.38 | 8.61 | 10.03 |

Result of UV analysis

λmax ($CH_3OH$) 251 nm.

(ξ11,700).

Result of $^1$H-NMR analysis ($CDlC_3$, TMS)

As shown in FIG. 2.

EXAMPLE 1

Preparation of 1-benzyl-5-(2,6-dimethylheptyl)imidazole

In 10 ml of ethanol was dissolved 0.6 g of 1-benzyl-5-[(E)-2,6-dimethyl-1,5-heptadienyl]imidazole obtained in Reference Example 1. To the solution was added 0.1 g of 10% palladium-carbon, and the mixture was subjected to ctalytic reduction under atmospheric pressure. After a theoretical amount of hydrogen was consumed, the catalyst was filtered off and the filtrate was concentrated under reduced pressure. The residue was recrystallized from hexane, giving the title compound in a yield of 95%.

Melting point 61°–62° C.

Result of $^1$H-NMR analysis

Figure 3:
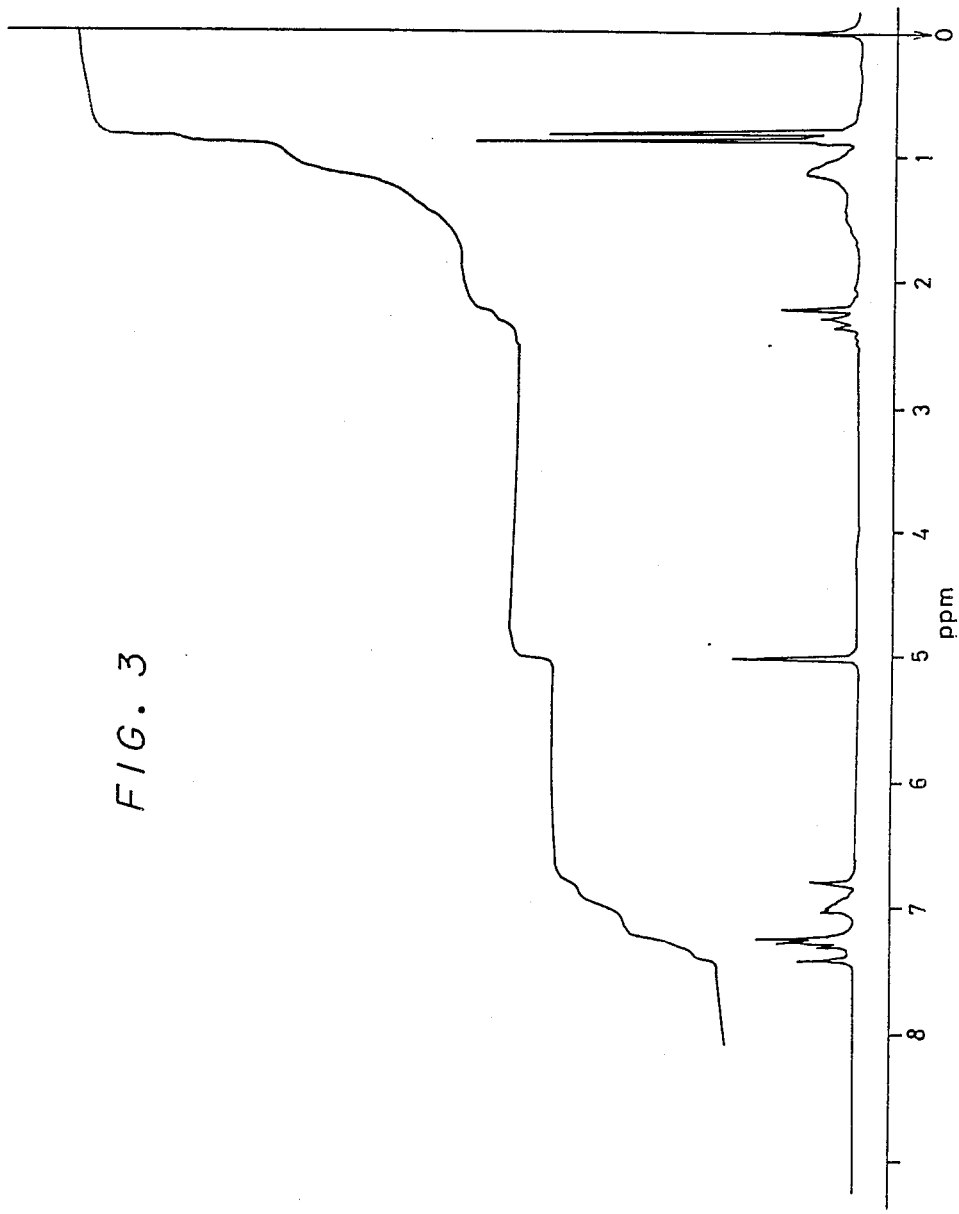

FIG. 3 shows the result obtained using TMS as an internal standard substance in $CDCl_3$.

The title compound can be also prepared from the 1-benzyl-5-[(Z)-2,6-dimethyl-1,5-heptadienyl]imidazole obtained in Reference Example 1.

EXAMPLE 2

Preparation of
1-methyl-5-[(E)-2,6-dimethyl-1,5heptadienyl]-imidazole

In 15 ml of dichloromethane were dissolved 1 g of methylamine hydrochloride, 1.5 g of triethylamine and 1.1 g of citral. Anhydrous magnesium sulfate (5 g) was added to the solution and the mixture was refluxed with heating for 3 hours. After filtering off the magnesium sulfate, the filtrate was concentrated under reduced pressure. The imine compound thus obtained was dissolved in 15 ml of dried methanol. To the solution were consecutively added 5 g of anhydrous potassium carbonate and 2.5 g of TosMIC. The mixture was refluxed with heating for 3 hours. After cooling, the solvent was distilled off from the reaction mixture under reduced pressure and the residue was extracted with ether. The ether layer was washed with a saline solution after which the layer was dried over anhydrous sodium sulfate. The solvent was distilled off under reduced pressure. The residue was purified by silica gel column chromatography. The elution was conducted first with hexane-ethyl acetate (3:1) and then with hexane-ethyl acetate (1:1). The contemplated compound was eluted with hexane-ethyl acetate (1:1). The solvent was distilled off from the eluate under reduced pressure, giving the desired compound (yield 12%).

Result of $^1$H-NMR analysis

Figure 4:
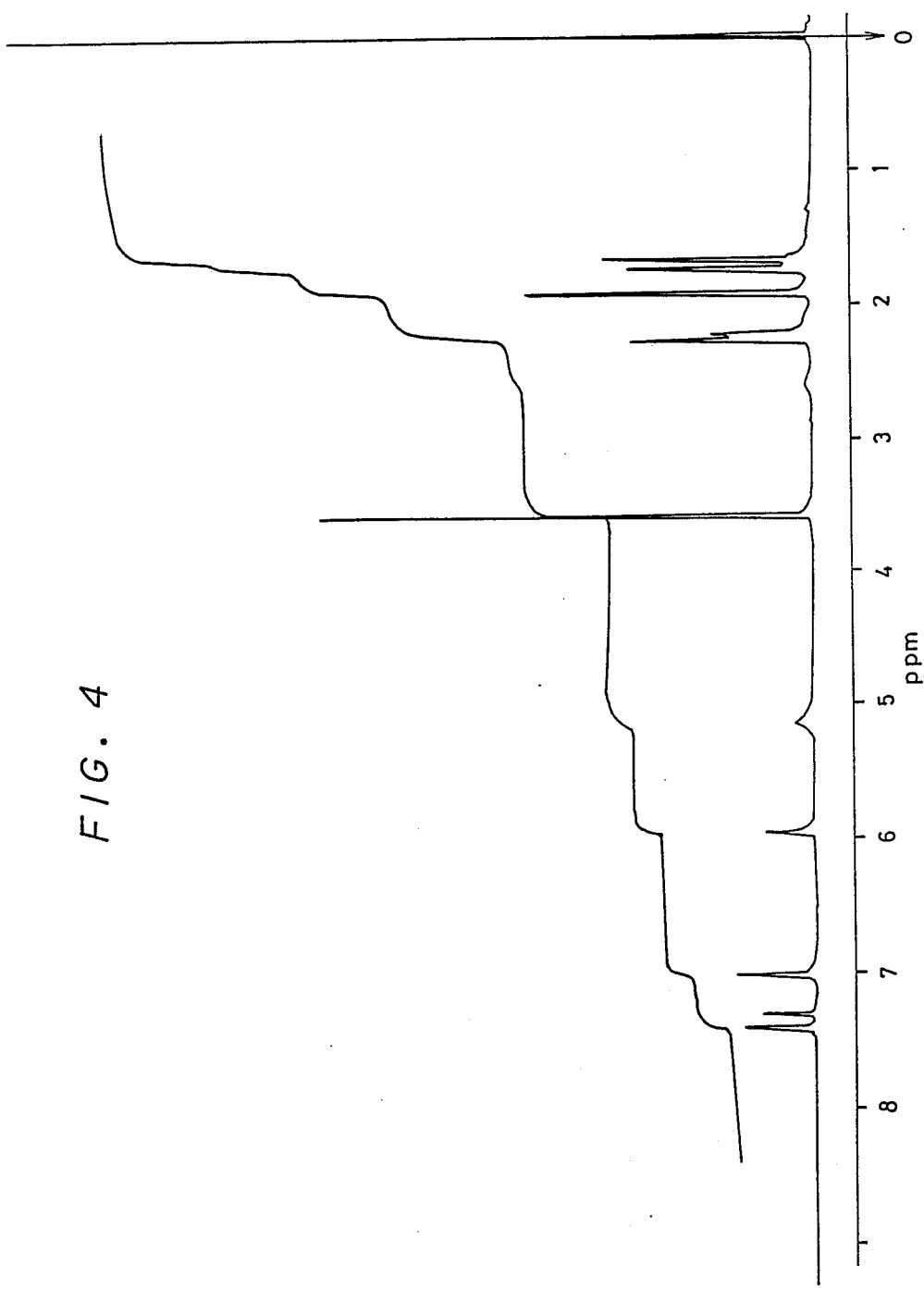

FIG. 4 shows the result obtained using TMS as an internal standard substance in CDC1$_3$

EXAMPLE 3

Preparation of
1-ethyl-5-[(E)-2,6-dimethyl-1,5-heptadienyl]imidazole

The same procedure as in Example 2 was repeated with the exception of using ethylamine hydrochloride in place of the methylamine hydrochloride used in Example 2, producing the title compound.

Result of $^1$H-NMR analysis

Figure 5:
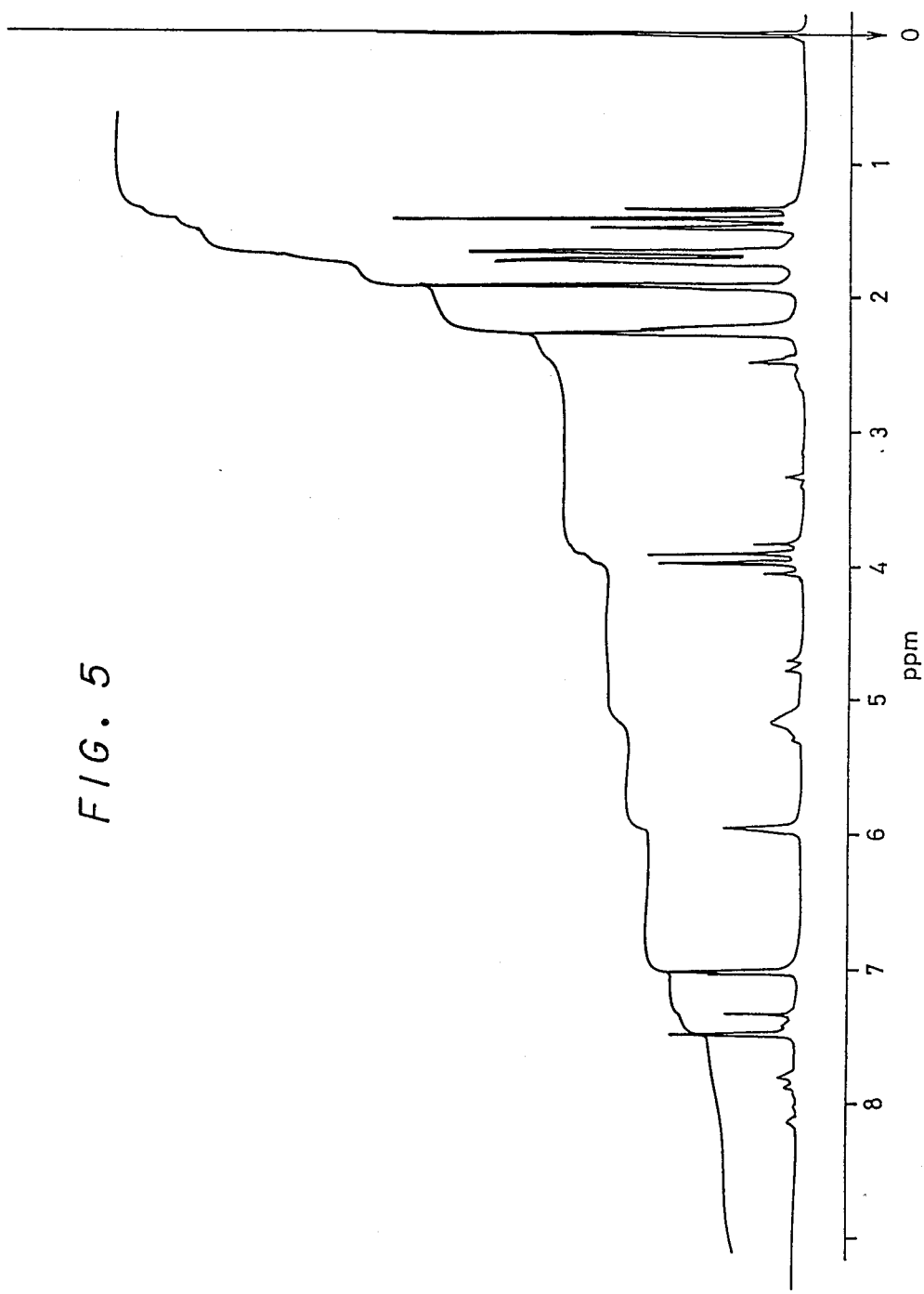

FIG. 5 shows the result obtained using TMS as an internal standard substance in CDCl$_3$.

EXAMPLE 4

Preparation of
1-propyl-5-[(E)-2,6-dimethyl-1,5-heptadienyl]imidazole

The same procedure as in Example 2 was repeated with the exception of using n-propylamine in place of the methylamine hydrochloride used in Example 2, producing the title compound.

Result of $^1$H-NMR analysis

Figure 6:
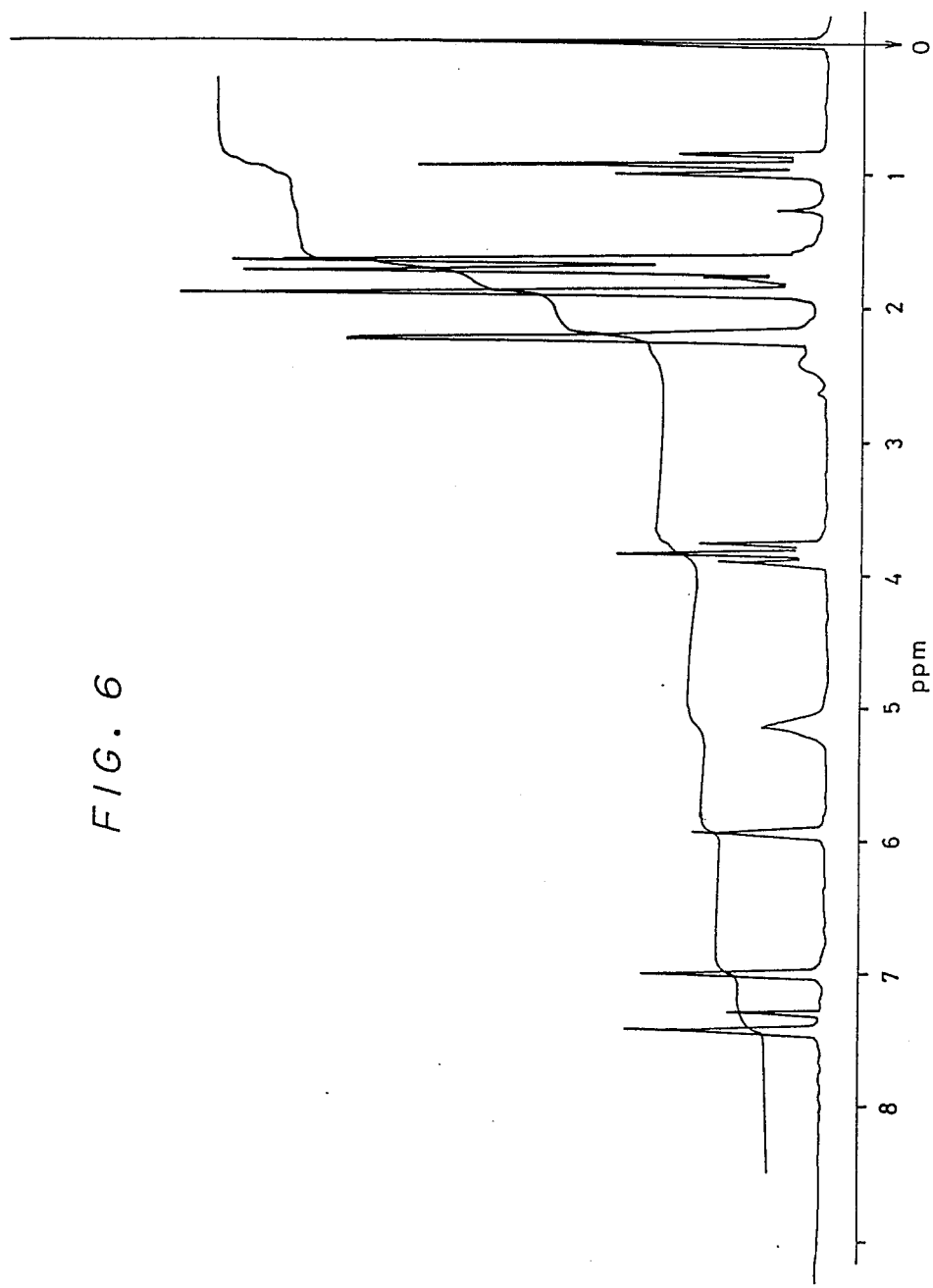

FIG. 6 shows the result obtained using TMS as an internal standard substance in CDCl$_3$.

EXAMPLE 5

Preparation of
1-butyl-5-[(E)-2,6-dimethyl-1,5-heptadienyl]imidazole

The same procedure as in Example 2 was repeated with the exception of using n-butylamine in place of the methylamine hydrochloride used in Example 2, producing the title compound.

Result of $^1$H-NMR analysis

Figure 7:
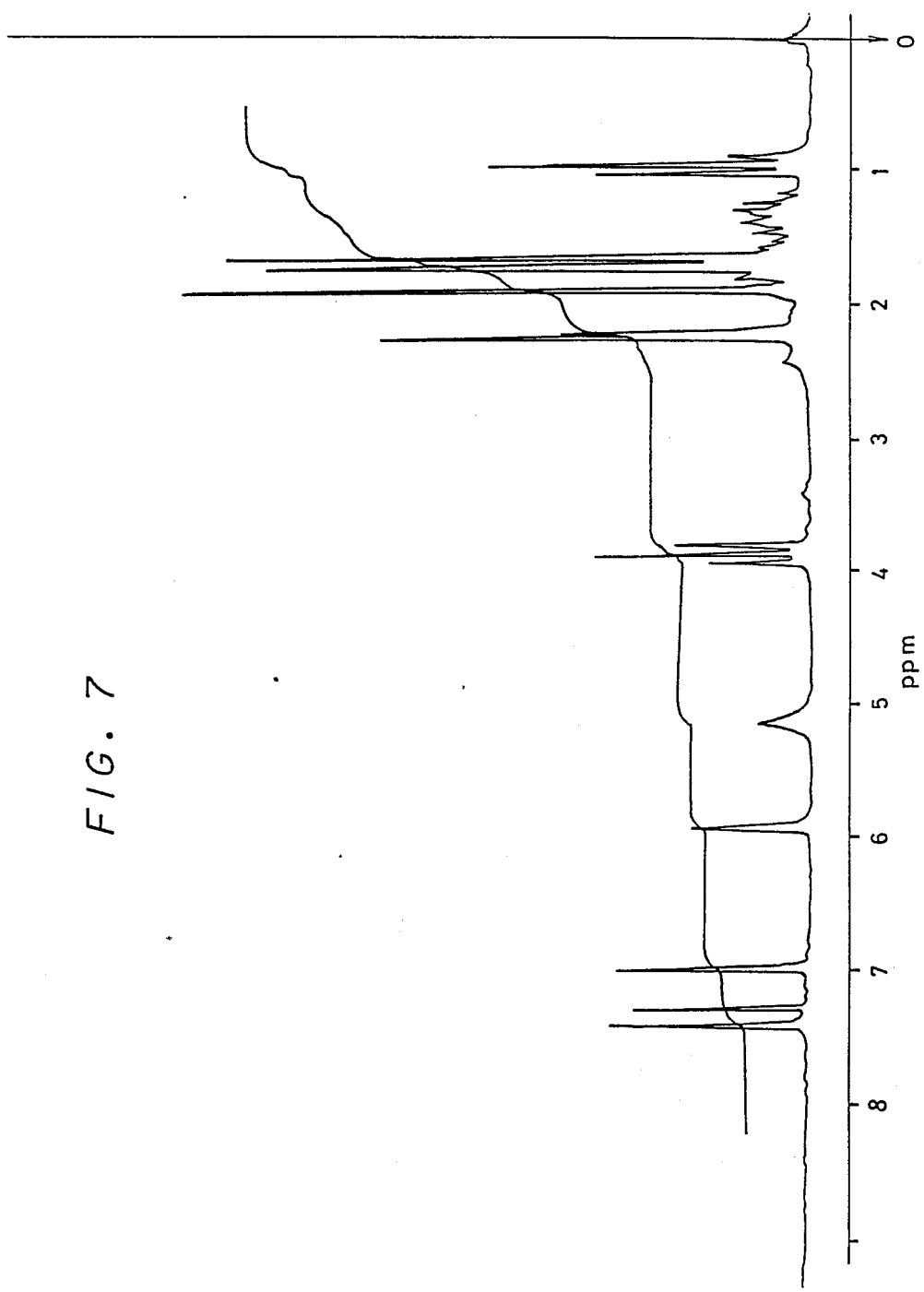

FIG. 7 shows the result obtained using TMS as an internal standard substance in CDCl$_3$.

EXAMPLE 6

Preparation of
1-amyl-5-[(E)-2,6-dimethyl-1,5-heptadienyl]imidazole

The same procedure as in Example 2 was repeated with the exception of using n-amylamine in place of the methylamine hydrochloride used in Example 2, producing the title compound.

Result of $^1$H-NMR analysis

Figure 8:
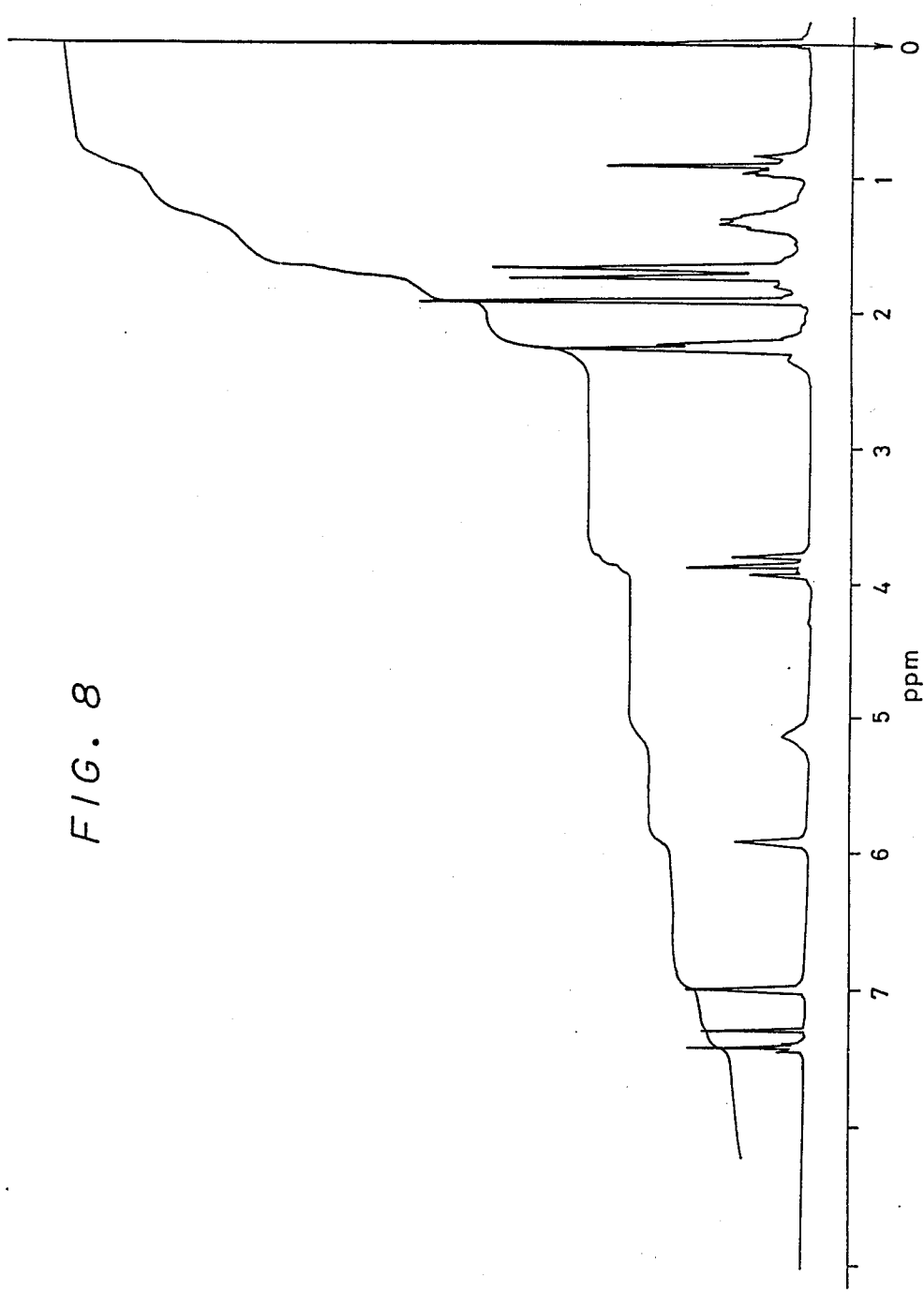

FIG. 8 shows the result obtained using TMS as an internal standard substance in CDCl$_3$.

EXAMPLE 7

Preparation of
1-hexyl-5-[(E)-2,6-dimethyl-1,5-heptadienyl]imidazole

The same procedure as in Example 2 was repeated with the exception of using n-hexylamine hydrochloride in place of the methylamine hydrochloride used in Example 2, producing the title compound.

Result of $^1$H-NMR analysis

Figure 9:
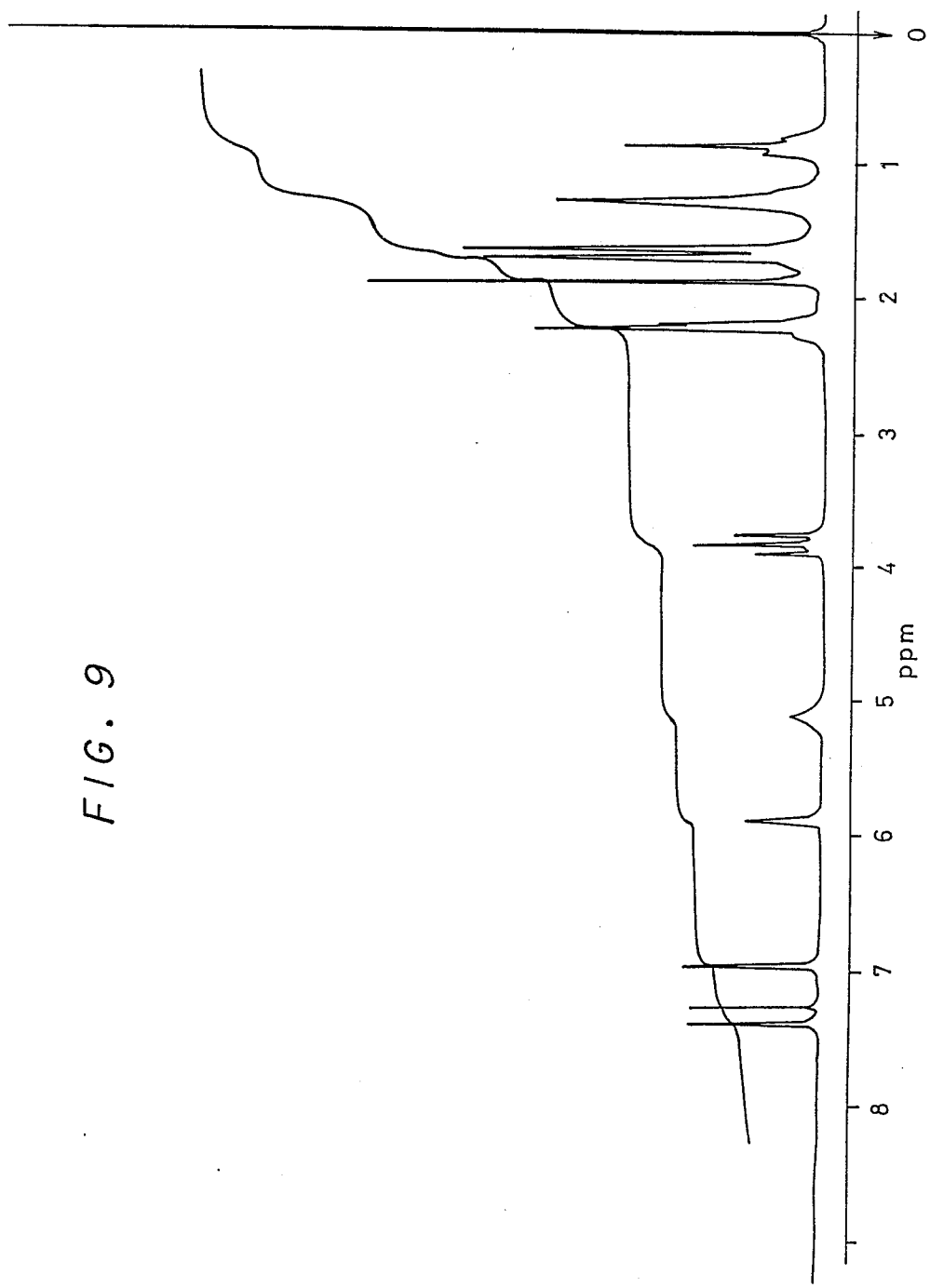

FIG. 9 shows the result obtained using TMS as an internal standard substance in CDCl$_3$.

EXAMPLE 8

Preparation of
1-isopropyl-5-[(E)-2,6-dimethyl-1,5-heptadienyl]imidazole

The same procedure as in Example 2 was repeated with the exception of using isopropylamine in place of the methylamine hydrochloride used in Example 2, producing the title compound.

Result of $^1$H-NMR analysis

Figure 10:
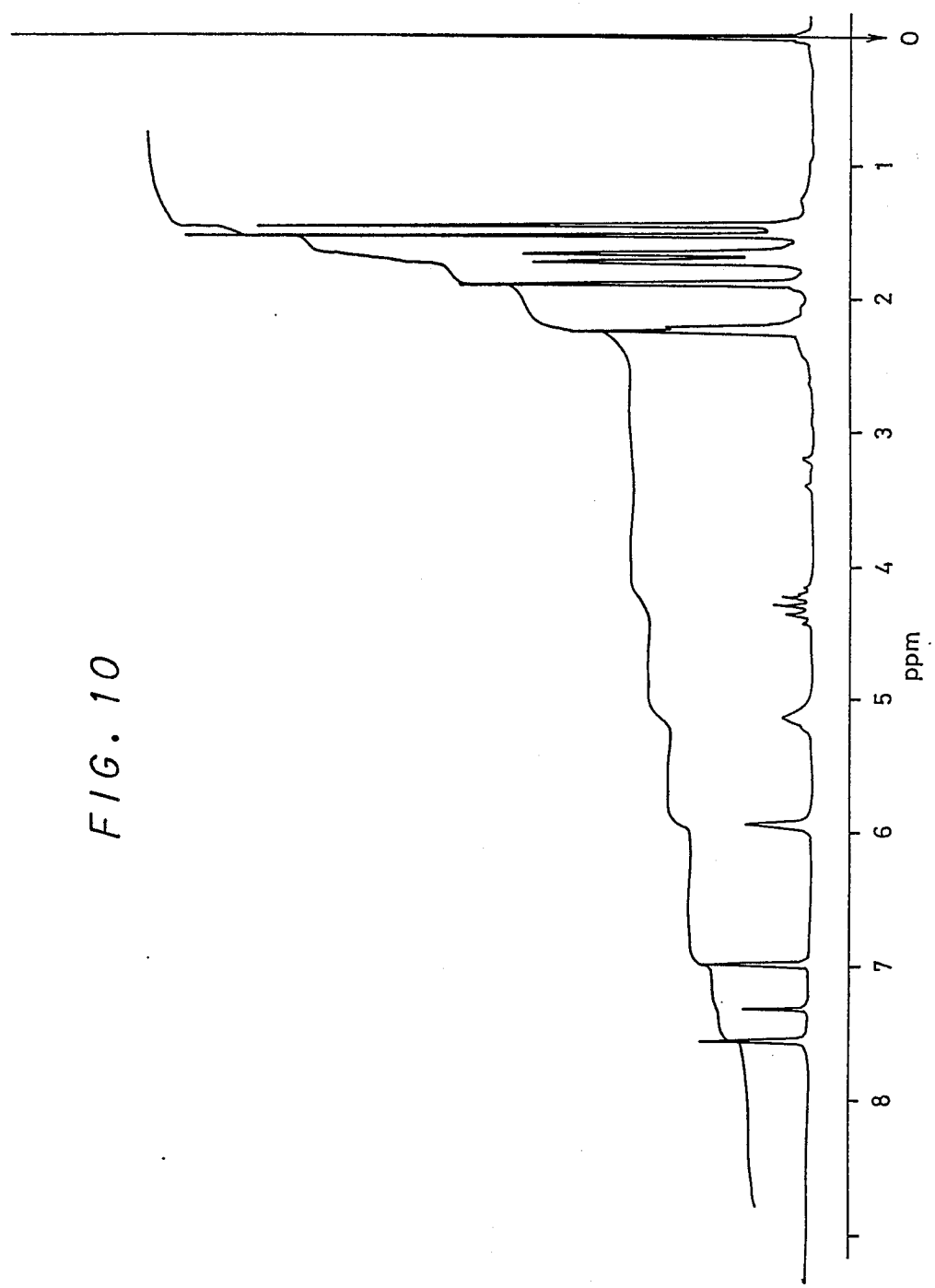

FIG. 10 shows the result obtained using TMS as an internal standard substance in CDCl$_3$.

EXAMPLE 9

Preparation of
1-isobutyl-5-[(E)-2,6-dimethyl-1,5-heptadienyl]imidazole

The same procedure as in Example 2 was repeated with the exception of using isobutylamine in place of the methylamine hydrochloride used in Example 2, producing the title compound.

Result of $^1$H-NMR analysis

Figure 11:
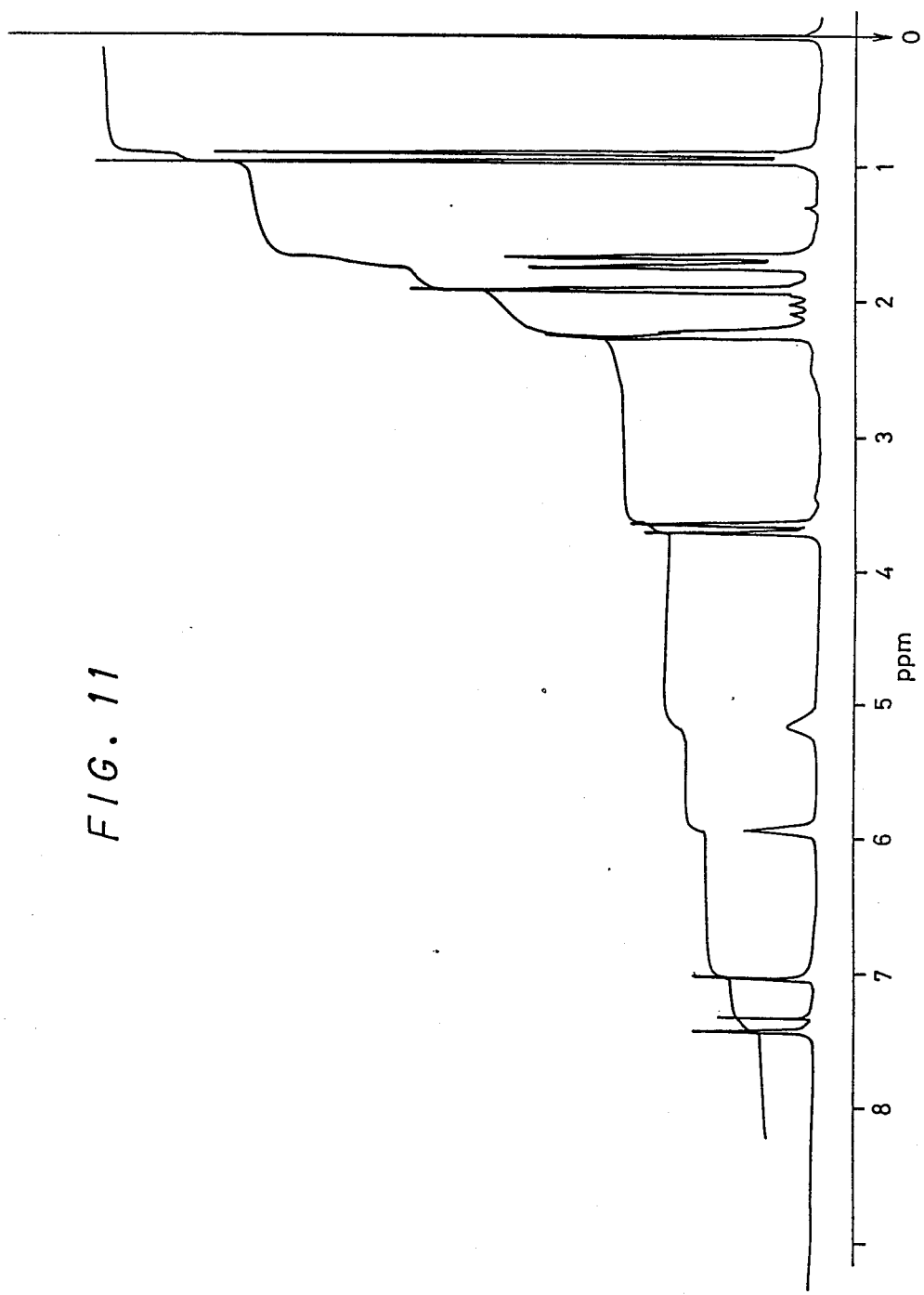

FIG. 11 shows the result obtained using TMS as an internal standard substance in CDCl$_3$.

EXAMPLE 10

Preparation of
1-sec-butyl-5-[(E)-2,6-dimethyl-1,5-heptadienyl]imidazole

The same procedure as in Example 2 was repeated with the exception of using sec-butylamine in place of the methylamine hydrochloride used in Example 2, producing the title compound.

Result of $^1$H-NMR analysis

Figure 12:
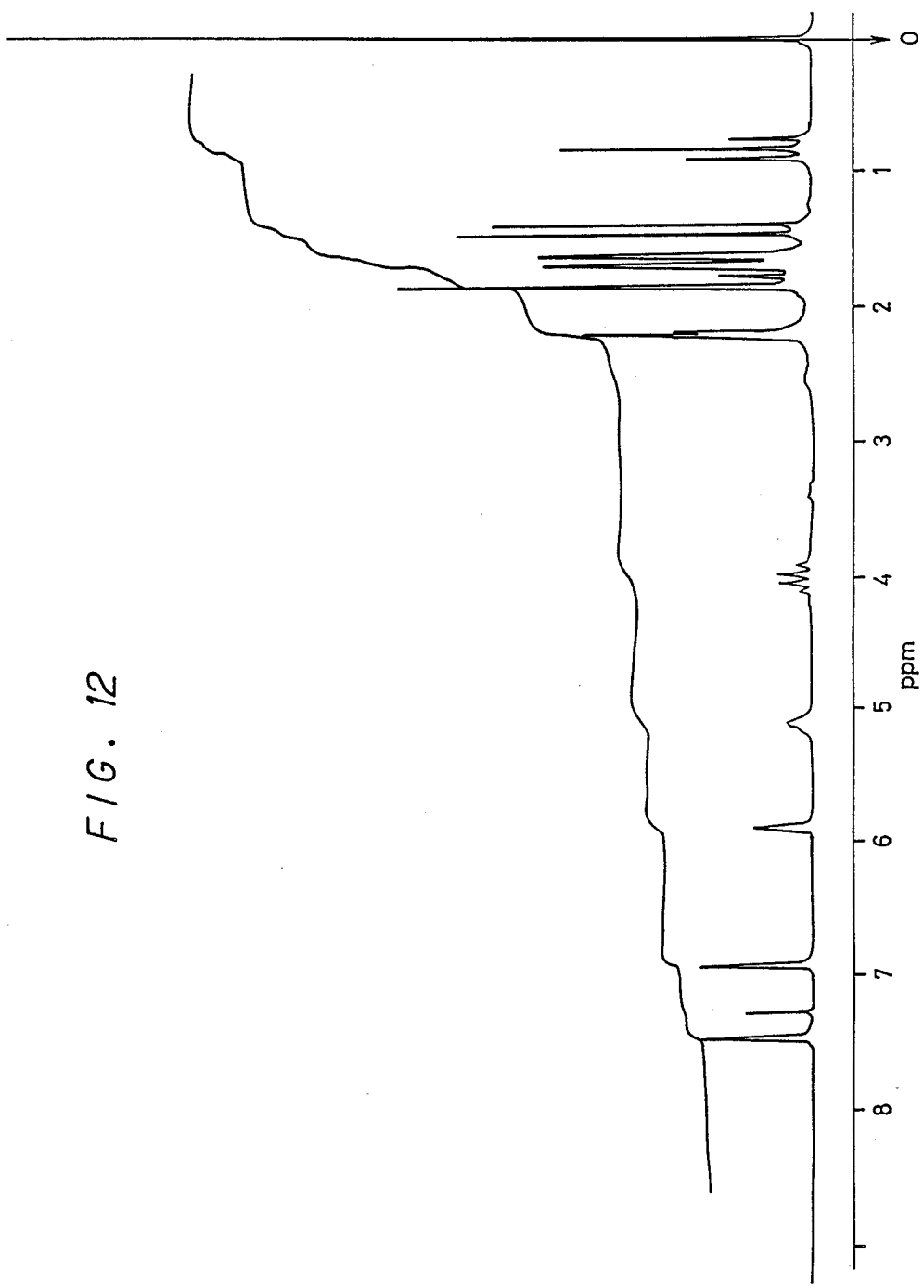

FIG. 12 shows the result obtained using TMS as an internal standard substance in CDCl$_3$.

EXAMPLE 11

Preparation of
1-isoamyl-5-[(E)-2,6-dimethyl-1,5-heptadienyl]imidazole

The same procedure as in Example 2 was repeated with the exception of using isoamylamine hydrocholride in place of the methylamine hydrochloride used in Example 2, producing the title compound.

Result of $^1$H-NMR analysis

Figure 13:
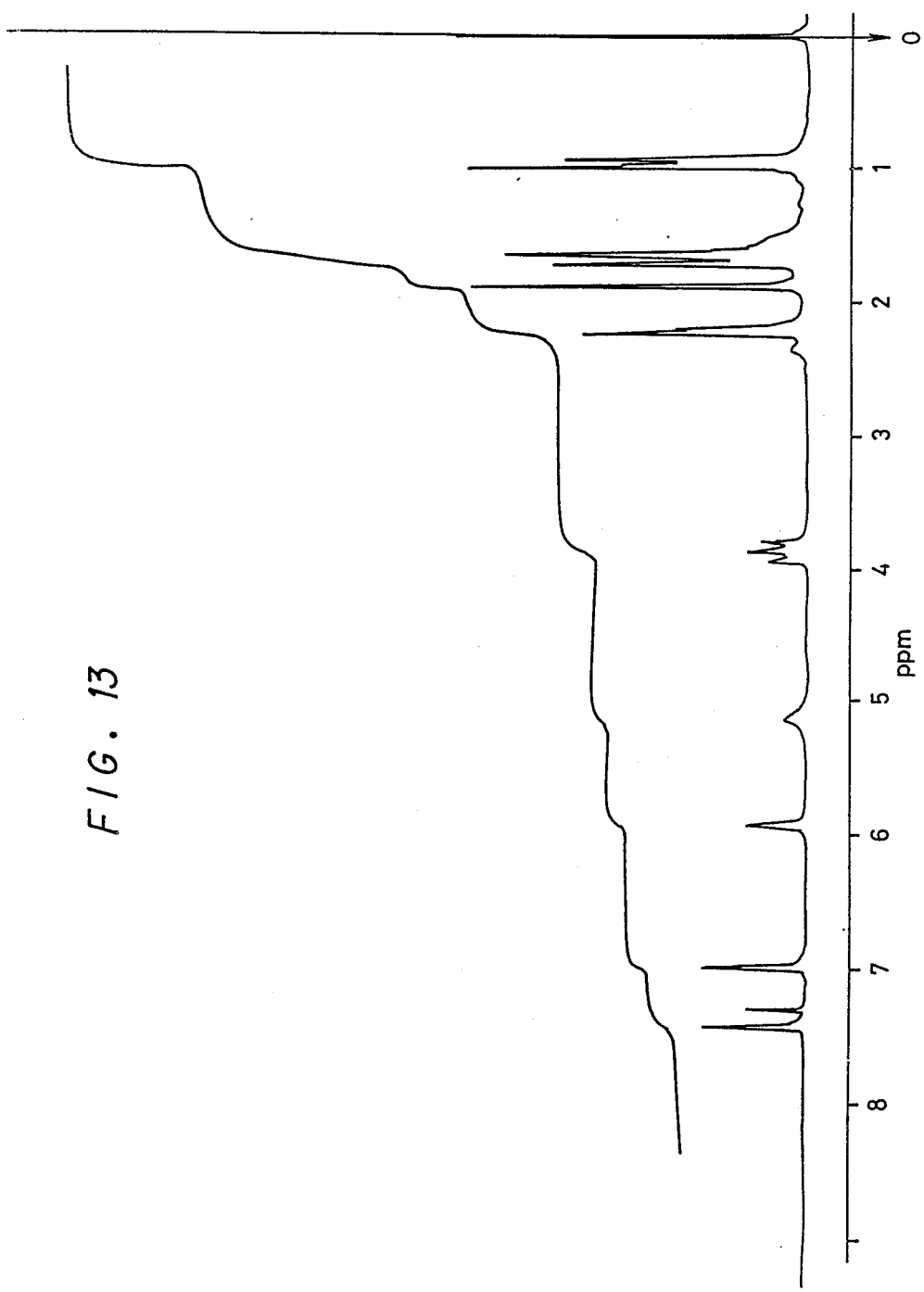

FIG. 13 shows the result obtained using TMS as an internal standard substance in $CDCl_3$.

EXAMPLE 12

Preparation of 1-cyclopentyl-5-[(E)-2,6-dimethyl-1,5-heptadienyl-]imidazole

The same procedure as in Example 2 was repeated with the exception of using cyclopentylamine in place of the methylamine hydrochloride used in Example 2, producing the title compound.

Result of $^1$H-NMR analysis

Figure 14:
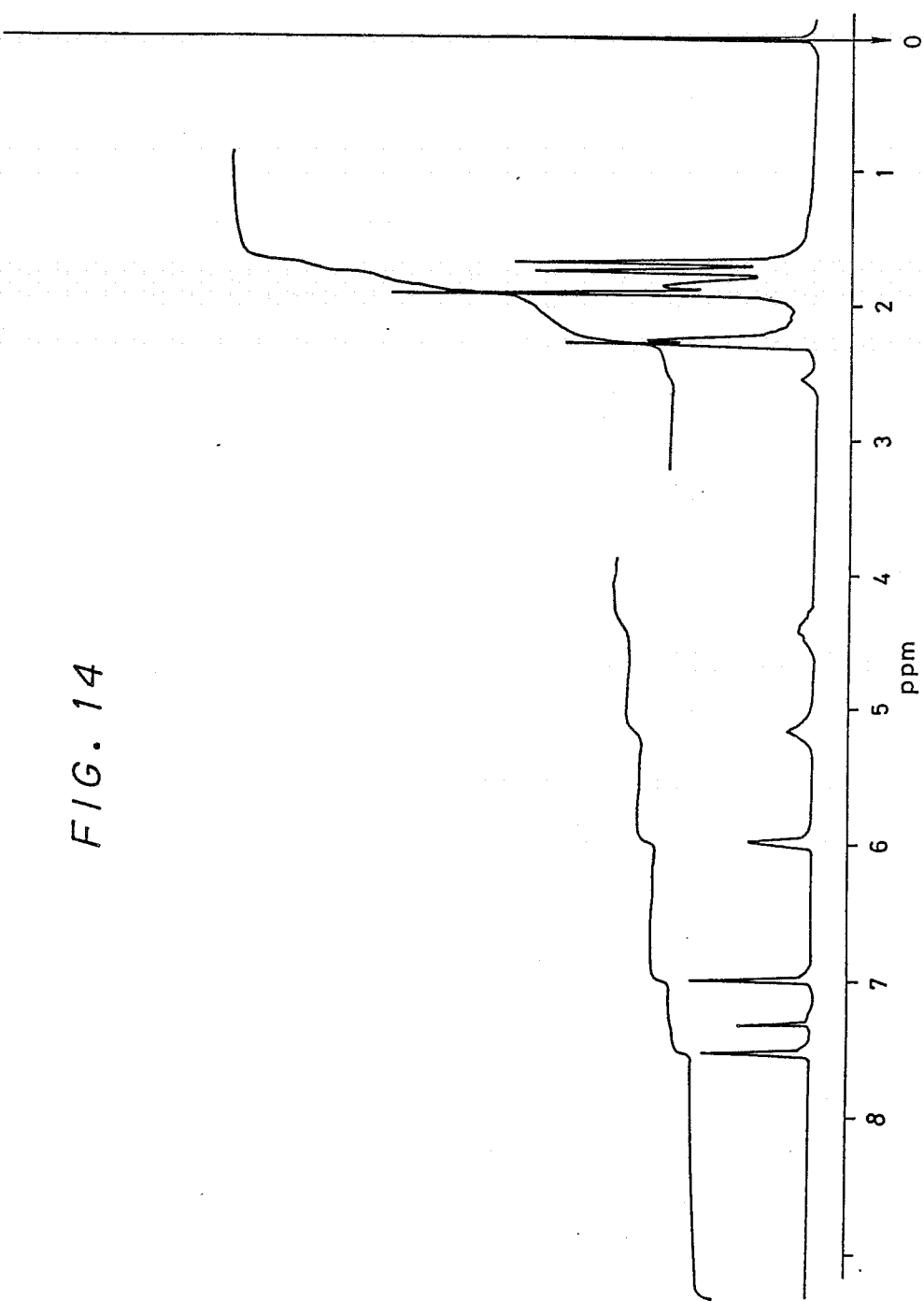

FIG. 14 shows the result obtained using TMS as an internal standard substance in $CDCl_3$.

EXAMPLE 13

Preparation of 1-cyclohexyl-5-[(E)-2,6-dimethyl-1,5-heptadienyl-]imidazole

The same procedure as in Example 2 was repeated with the exception of using cyclohexylamine in place of the methylamine hydrochloride used in Example 2, producing the title compound.

Result of $^1$H-NMR analysis

Figure 15:
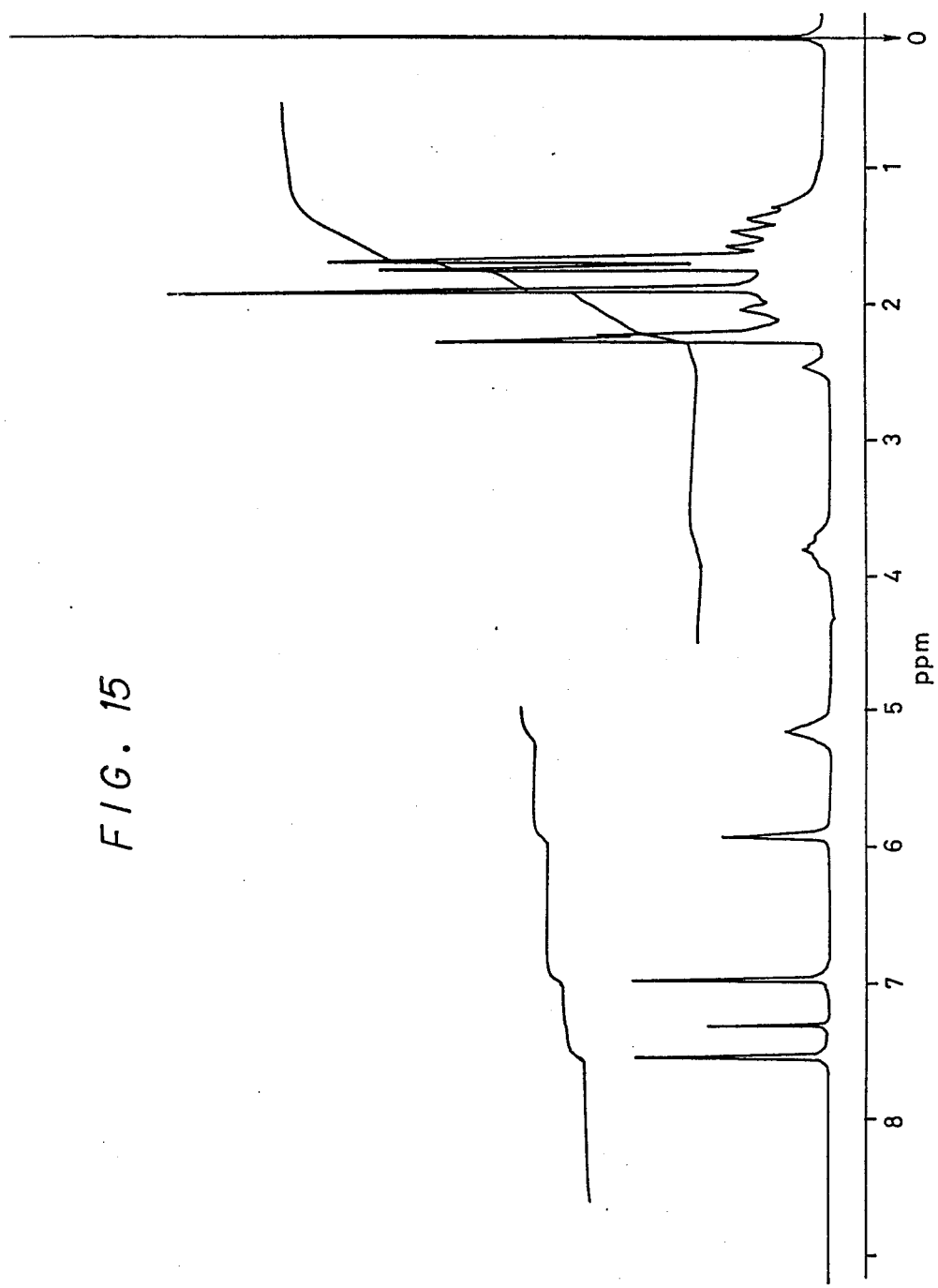

FIG. 15 shows the result obtained using TMS as an internal standard substance in $CDCl_3$.

The yields of contemplated compounds prepared by the processes described in Examples 3 to 13 were in the range of 10 to 30%.

Given below are Test Examples for testing the compounds of the present invention for biological activity and for noxious insects-repelling or -controlling effect.

[Anti-JH Activity Test I]

The compound (test preparation) of the present invention diluted with acetone to the predetermined concentration was applied dropwise, in an amount of 1 to 4 μper larva, to the abdomen and the back of third- or fourth-instar larvae (those living for 0 to 8 hours after ecdysis) of household silkworms (*Bombyx mori*) raised in a room and fed on mulberry leaves. Immediately after treatment, the larvae were placed into a plastics case and reared by being fed on mulberry leaves until they started spinning cocoons. The anti-JH activity was evaluated in terms of the percentage (%) of presence of larvae (premature larvae) which began to spin cocoons at the 4th-instar stage without undergoing the 5th-instar moult. The test larvae treated with each test preparation in each group numbered 20. The test larvae in the control group treated with acetone in lieu of the test compound all commenced cocooning after the 5th-instar moult.

Table 1 below shows the results of the test conducted using, as the test preparation, the compound of the invention obtained in Example 1.

TABLE 1

| | Activity to induce premature metamorphosis (%) | | | | | |
|---|---|---|---|---|---|---|
| | 3rd-instar larvae | | | 4th-instar larvae | | |
| Dosage (μg/larva) | 2 | 1 | 0.5 | 10 | 2 | 1 |
| Compound of this invention | 100 | 70 | 10 | 100 | 100 | 20 |

TABLE 1-continued

| Activity to induce premature metamorphosis (%) | |
|---|---|
| 3rd-instar larvae | 4th-instar larvae |

Table 1 above shows that the compound obtained in Example 1 had an anti-JH activity.

Investigation was conducted to determine whether the activity of the foregoing compound of the invention can be inhibited by methoprene which is a JH-active substance. It was found that the activity thereof was completely inhibited by the substance. [Anti-JH Activity Test II]

After the test compound diluted to the predetermined concentration was applied dropwise to 4th-instar household silkworm larvae in the same manner as in Anti-JH Activity Test I as described above, the larvae thus treated were reared until they started cocooning. The number of larvae which began to cocoon at the 4th-instar stage without undergoing the 5th-instar moult were counted to determine the percentage (%) of presence of larvae (premature larvae). Then the concentration of test preparation which induced 50% presence was determined and indicated as an anti-JH activity value ($ED_{50}$).

Table 2 shows the results obtained using the compounds of the invention prepared in Examples 1 to 13.

TABLE 2

| Test Compound | $ED_{50}$ (μg/larva) |
|---|---|
| Compound obtained in Example 1 | 1.4 |
| Compound obtained in Example 2 | 17.5 |
| Compound obtained in Example 3 | 5.8 |
| Compound obtained in Example 4 | 3.5 |
| Compound obtained in Example 5 | 3.1 |
| Compound obtained in Example 6 | 2.4 |
| Compound obtained in Example 7 | 4.2 |
| Compound obtained in Example 8 | 6.4 |
| Compound obtained in Example 9 | 1.8 |
| Compound obtained in Example 10 | 1.9 |
| Compound obtained in Example 11 | 3.5 |
| Compound obtained in Example 12 | 3.6 |
| Compound obtained in Example 13 | 6.6 |

Table 2 reveals that all the compounds of the invention prepared in Examples 1 to 13 had an anti-JH activity and were useful as an anti-JH active agent.

[Test for Vermin-Repelling and -Killing Effect]

A 2 m quantity of a medium was placed onto each Petri dish of plastics having a 30 mm diameter onto which the compound of the invention diluted with ethanol to the predetermined concentration (1000 to 0.0001 ppm) was poured so that the final ethanol concentration in the medium was 1% or less.

Five nematodes were put onto each of the dishes and the number was counted of insects which died or survived and which agonized or abnormally or normally behaved, all after 24 hours. Those further survived were transferred to a casing for normal rearing after which the number of hatched young larvae living 4 days later was determined. Each test was performed at room temperature.

The test results show the following. Although even the compounds of the invention in a high concentration of 100 ppm or more were virtually unable to promptly kill the insects, those of 1000 to 0.001 ppm in concentration caused insects to agonize or abnormally behave. The number of hatched young larvae alive after 4 days apparently decreased among the insects treated with any of the compounds of the invention in a concentration of 10 ppm or more. This shows that the compounds of the present invention are effective in repelling or killing noxious insects.

We claim:

1. A 1,5-disubstituted imidazole represented by the formula (1)

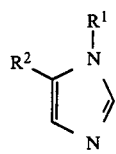

wherein $R^1$ is a lower alkyl group, a cycloalkyl group having 3 to 8 carbon atoms or a phenyl lower alkyl group, and $R^2$ is a 2,6-dimethyl-1,5-heptadienyl group or a 2,6-dimethylheptyl group, except for a compound wherein $R^1$ is a phenyl lower alkyl group and $R^2$ is a 2,6-dimethyl-1,5-heptadienyl group, or an acid addition salt thereof.

2. A 1,5-disubstituted imidazole according to claim 1 which is a compound represented by the formula (1A)

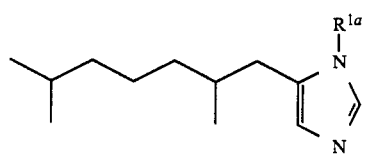

wherein $R^{1a}$ is a phenyl lower alkyl group, or an acid addition salt thereof.

3. A 1,5-disubstituted imidazole according to claim 2 which is a 1-benzyl-5-(2,6dimethylheptyl)imidazole or an acid addition salt thereof.

4. A 1,5-disubstituted imidazole according to claim 1 which is a compound represented by the formula (1B)

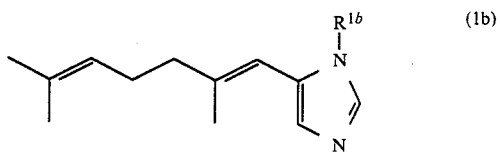

wherein $R^{1b}$ is a lower alkyl group or a cycloalkyl group having 3 to 8 carbon atoms or an acid addition salt thereof.

5. A 1,5-disubstituted imidazole according to claim 4 which is selected from the group consisting of: 1-methyl-5-(2,6-dimethyl-1,5-heptadienyl)imidazole, 1-ethyl-5-(2,6-dimethyl-1,5-heptadienyl)imidazole, 1-propyl 5-(2,6-dimethyl-1,5-heptadienyl)imidazole, 1-butyl-5-(2,6-dimethyl-1,5-heptadienyl)imidazole, 1-amyl-5-(2,6-dimethyl-1,5-heptadienyl)imidazole, 1-hexyl-5-(2,6-dimethyl-1,5-heptadienyl)imidazole, 1-isopropyl-5-(2,6-dimethyl-1,5-heptadienyl)imidazole, 1-isobutyl-5-(2,6-dimethyl-1,5-heptadienyl)imidazole, 1-sec-butyl-5-(2,6-dimethyl-1,5-heptadienyl)imidazole, 1-isoamyl-5-(2,6-dimethyl-1,5-heptadienyl)imidazole, 1-cyclopentyl-5-(2,6-dimethyl-1,5-heptadienyl)-imidazole and 1-cyclohexyl-5-(2,6-dimethyl-1,5-heptadienyl)imidazole, and acid additiion salts thereof.

6. A composition for inhibiting the activity of the juvenile hormone in insects, said composition comprising a carrier and an amount effective for inhibiting said hormone of an active ingredient which is a 1,5-disubstituted imidazole represented by the formula

wherein $R^1$ is a lower alkyl group, a cycloalkyl group having 3 to 8 carbon atoms or a phenyl lower alkyl group, and $R^2$ is a 2,6-dimethyl-1,5-heptadienyl group or a 2,6-dimethylheptyl group, except for a compound wherein $R^1$ is a phenyl lower alkyl group and $R^2$ is a 2,6-dimethyl-1,5-heptadienyl group, or an acid addition salt thereof.

* * * * *